US012403120B2

(12) United States Patent
Muntendam

(10) Patent No.: US 12,403,120 B2
(45) Date of Patent: Sep. 2, 2025

(54) PHARMACEUTICAL COMPOSITIONS OF FUROSEMIDE AND USES THEREOF

(71) Applicant: SQ Innovation AG, Zug (CH)

(72) Inventor: Pieter Muntendam, Boxford, MA (US)

(73) Assignee: SQ Innovation AG, Zug (CH)

( * ) Notice: Subject to any disclaimer, the term of this patent is extended or adjusted under 35 U.S.C. 154(b) by 762 days.

(21) Appl. No.: 17/311,634

(22) PCT Filed: Dec. 10, 2019

(86) PCT No.: PCT/EP2019/084446
§ 371 (c)(1),
(2) Date: Jun. 7, 2021

(87) PCT Pub. No.: WO2020/120482
PCT Pub. Date: Jun. 18, 2020

(65) Prior Publication Data
US 2022/0008374 A1    Jan. 13, 2022

Related U.S. Application Data

(60) Provisional application No. 62/777,384, filed on Dec. 10, 2018.

(51) Int. Cl.
A61K 31/341    (2006.01)
A61K 9/00      (2006.01)
A61K 9/08      (2006.01)
A61K 31/635    (2006.01)
A61K 47/18     (2017.01)

(52) U.S. Cl.
CPC ............. A61K 31/341 (2013.01); A61K 9/08 (2013.01); A61K 47/18 (2013.01)

(58) Field of Classification Search
CPC ...... A61K 31/341; A61K 31/635; A61K 9/08; A61K 9/0019; A61K 47/18
See application file for complete search history.

(56) References Cited

U.S. PATENT DOCUMENTS

| | | | |
|---|---|---|---|
| 4,663,348 A | 5/1987 | Chafetz et al. | |
| 4,698,361 A | 10/1987 | Di Schiena | |
| 5,134,127 A | 7/1992 | Stella et al. | |
| 5,376,645 A | 12/1994 | Stella et al. | |
| 5,633,240 A | 5/1997 | Ranade | |
| 5,814,623 A | 9/1998 | Ranade | |
| 8,241,661 B1 | 8/2012 | Fuisz et al. | |
| 8,282,366 B2 | 10/2012 | Hilber et al. | |
| 8,372,809 B2 | 2/2013 | Unemori et al. | |
| 8,414,532 B2 | 4/2013 | Brandt et al. | |
| 9,884,039 B2 | 2/2018 | Michaels et al. | |
| 10,272,064 B2 | 4/2019 | Michaels et al. | |
| 10,391,105 B2 | 8/2019 | Cashman et al. | |
| 11,246,851 B2 | 2/2022 | Muntendam | |
| 2008/0076828 A1 | 3/2008 | Dalton et al. | |
| 2009/0233951 A1 | 9/2009 | Somberg et al. | |
| 2011/0060280 A1 | 3/2011 | Caffey et al. | |
| 2012/0077829 A1 | 3/2012 | Somberg et al. | |
| 2013/0252932 A1 | 9/2013 | Seward | |
| 2016/0051507 A1 | 2/2016 | Michaels et al. | |
| 2018/0303790 A1 | 10/2018 | Michaels et al. | |
| 2020/0038364 A1 | 2/2020 | Michaels et al. | |

FOREIGN PATENT DOCUMENTS

| | | | |
|---|---|---|---|
| CA | 2685331 C | 7/2016 | |
| CN | 1477977 A | 2/2004 | |
| EP | 080195 A1 | 6/1983 | |
| EP | 1078636 A1 | 2/2001 | |
| WO | WO-1992021769 A1 | 12/1992 | |
| WO | WO-1996006615 A1 | 3/1996 | |
| WO | WO-2002038186 A1 | 5/2002 | |
| WO | WO-2009140659 A1 | 11/2009 | |
| WO | WO-2010030667 A1 | 3/2010 | |
| WO | WO-2014165660 A1 * | 10/2014 | ........... A61K 31/341 |

OTHER PUBLICATIONS

U.S. Appl. No. 17/668,519, filed Feb. 10, 2022, Pharmaceutical Compositions of Furosemide and Uses Thereof.
U.S. Appl. No. 17/414,160, filed Jun. 15, 2021, Pharmaceutical Compositions of Torsemide and U.
Ammar et al., "Inclusion complexation of furosemide in cyclodextrins: Part 1. Effect of cyclodextrins on the physicochemical characteristics of furosemide," *Pharmazie*,, vol. 54, No. 2, pp. 142-144 (1999).
Captisol Safety Data Sheet, dated Feb. 4, 2016, 2 pages.
El-Shenawy et al., "Enhancement of Solubility and Dissolution Rate of Torsemide as Poorly Soluble Loop Diuretic by Inclusion Complexation with both ß-Cyclodextrin and Hydroxypropyl-ß-Cyclodextrin," *Ijppr.Human*, vol. 7, pp. 221-235 (2016).
Garnero et al., "Improving furosemide polymorphs properties through supramolecular complexes of ß-cyclodextrin," *Journal of Pharmaceutical and Biomedical Analysis*, vol. 95, pp. 139-145 (2014).
International Search Report and Written Opinion of the International Searching Authority, the European Patent Office, for International Application No. PCT/EP2019/084446, dated Mar. 17, 2020, 10 pages.

(Continued)

Primary Examiner — Joseph K McKane
Assistant Examiner — Sagar Patel
(74) Attorney, Agent, or Firm — Dechert LLP

(57) ABSTRACT

A pharmaceutical composition and a method of administering the pharmaceutical composition to a patient suffering from edema, heart failure, kidney or liver disease or having symptoms thereof is disclosed. The pharmaceutical composition includes furosemide, or a pharmaceutically acceptable salt, hydrate or ester thereof and tris(hydroxymethyl)aminomethane. The furosemide is present in the pharmaceutical composition at a concentration from about 10 mg/mL to about 30 mg/mL and the tris(hydroxymethyl)aminomethane is present at a concentration of less than or equal to 40 mM. The pH value of the pharmaceutical composition is maintained between about 8.0 and about 8.5 for parenteral administration.

26 Claims, 2 Drawing Sheets

(56) References Cited

OTHER PUBLICATIONS

International Search Report and Written Opinion of the International Searching Authority, the European Patent Office, for International Application No. PCT/EP2020/050098, dated Mar. 25, 2020, 13 pages.

Jain et al., "Sulfobutyl Ether7 ß-Cyclodextrin (SBE7 ß-CD) Carbamazepine Complex: Preparation, Characterization, Molecular Modeling, and Evaluation of In Vivo Anti-epileptic Activity," *AAPS PharmSciTech*, vol. 12, No. 4, ( 2011).

Ozdemir & Ordu, "Improvement of dissolution properties of furosemide by complexation with beta-cyclodextrin," *Drug Dev Ind Pharm* (1998) vol. 24(1), pp. 19-25 (Abstract only).

Press release entitled "Ligand and SQ Innovation Enter Into Exclusive Wordwide Captisol® License and Supply Agreements for High-Concentration Furosemide Formulation," dated Jul. 8, 2019, 5 pages.

Rowe, R.C., Sheskey, P.J. and Quinn, M.E., Handbook of Pharmaceutical Excipients, 6th Edition, *Pharmaceutical Press*, pp. 210-214 (2009).

Santos et al., "Stability of furosemide and aminophylline in parenteral solutions," *Brazilian Journal of Pharmaceutical Sciences*, vol. 47, pp. 89-96 (2011).

Sica et al., "Subcutaneous Furosemide in Heart Failure," *JACC: Basic to Translational Science*, vol. 3, No. 1, pp. 25-34 (2018).

Spamer et al., "Characterization of the complexes of furosemide with 2-hydroxypropyl-ß-cyclodextrin and sulfobutyl ether-7-ß-cyclodextrin," *European Journal of Pharmaceutical Sciences*, vol. 16, pp. 247-253 (2002).

\* cited by examiner

US 12,403,120 B2

PHARMACEUTICAL COMPOSITIONS OF FUROSEMIDE AND USES THEREOF

CROSS-REFERENCE TO RELATED APPLICATIONS

This application is the national stage application of International (PCT) Patent Application Serial No. PCT/EP2019/084446, filed Dec. 10, 2019, which claims the benefit of and priority to U.S. Provisional Patent Application Ser. No. 62/777,384, filed Dec. 10, 2018; the contents of these applications are hereby incorporated by reference in their entirety.

FIELD OF THE INVENTION

The present disclosure relates to pharmaceutical compositions containing furosemide and methods of administering the pharmaceutical compositions to a patient. More specifically, the present disclosure relates to pharmaceutical compositions containing furosemide and tris(hydroxymethyl)aminomethane.

BACKGROUND

Furosemide is a benzoic-sulfonamide-furan used as a potent loop diuretic with fast onset and short duration for the treatment of hypertension, edema and edema related conditions, such as congestive heart failure, cirrhosis of the liver or liver failure, and other renal diseases. Due to limited oral bioavailability, furosemide is typically administered intravenously or intramuscularly to patients with decompensated heart failure or other forms of advanced edema.

However, furosemide is poorly soluble and pharmaceutical formulations need to administer a typical clinical dose of 80 mg. A typical injectable formulation contains 8-10 mL solution. Increasing the concentration of furosemide to reduce the volume of administration impacts the stability of a pharmaceutical formulation and presents additional challenges.

Thus, a need exists for therapeutically effective improved pharmaceutical compositions containing furosemide suitable for use with, e.g., auto-injection devices and smaller minipumps.

SUMMARY

The present disclosure provides a pharmaceutical composition of furosemide with tris(hydroxymethyl)aminomethane ("Tris") at a concentration of less than or equal to 40 mM for administration at a pH value from about 8.0 to about 8.5 enabling a stable and higher concentration of furosemide in the composition.

In one aspect, the present disclosure provides the pharmaceutical composition including the furosemide or a pharmaceutically acceptable salt, hydrate or ester thereof, and the Tris at a concentration of less than or equal to 40 mM. The furosemide is present in the pharmaceutical composition at a concentration from about 10 mg/mL to about 30 mg/mL. The pharmaceutical composition has a pH value from about 8.0 and about 8.5. In some embodiments, the furosemide is present in the pharmaceutical composition at the concentration from about 16 mg/mL to about 26 mg/mL. In certain embodiments, the pH value of the pharmaceutical composition is from about 8.2 to about 8.5. In various embodiments, the pharmaceutical composition has a molar ratio of the Tris to the furosemide of less than or equal to 1.5.

In one embodiment, the molar ratio of the Tris to the furosemide in the pharmaceutical composition is from about 1 to about 1.5, and in another embodiment, the molar ratio is less than or equal to 0.8. In certain embodiments, the furosemide is present in the pharmaceutical composition at the concentration from about 16 mg/mL to about 20 mg/mL and the concentration of the Tris is less than or equal to 40 mM. Further, in certain embodiments, the pH value of the pharmaceutical composition is maintained from about 8.2 to about 8.5 and the molar ratio of the Tris to the furosemide is maintained from about 1 to about 1.5.

In another aspect, the present disclosure provides a method of treating a patient suffering from edema, heart failure, kidney or liver disease or having symptoms thereof. The method includes administering to the patient a therapeutically effective amount of a pharmaceutical composition comprising furosemide, or a pharmaceutically acceptable salt, hydrate or ester thereof and Tris. In some embodiments, the method includes administering furosemide at a concentration from about 10 mg/mL to about 24 mg/mL. In certain embodiments, the concentration of Tris is less than or equal to 40 mM. In various embodiments, the method includes administering the pharmaceutical composition at a pH value from about 8.0 and about 8.5.

In another aspect, the present disclosure provides a pharmaceutical composition, comprising: from about 60 mM to about 95 mM of a diuretic selected from the group consisting of 4-chloro-2-((furan-2-ylmethyl)amino)-5-sulfamoylbenzoic acid, a pharmaceutically acceptable salt thereof, and a mixture of the foregoing; from about 20 mM to about 30 mM of a buffer comprising tris(hydroxymethyl)aminomethane; and water; wherein the pharmaceutical composition has a pH value from about 8.0 to about 8.5. In some embodiments, the pharmaceutical composition comprises from about 80 mM to about 95 mM of the diuretic. In some embodiments, the pharmaceutical composition comprises about 91 mM of the diuretic. In some embodiments, the diuretic is a mixture of 4-chloro-2-((furan-2-ylmethyl)amino)-5-sulfamoylbenzoic acid and a pharmaceutically acceptable salt thereof. In some embodiments, the pharmaceutical composition comprises about 25 mM of a buffer comprising tris(hydroxymethyl)aminomethane. In some embodiments, said buffer is a mixture of tris(hydroxymethyl)aminomethane and a pharmaceutically acceptable salt thereof. In some embodiments, the pharmaceutical composition has a pH of from about 8.2 to about 8.5.

In another aspect, the present disclosure provides a method of treating a patient suffering from a condition selected from edema, heart failure, kidney disease, or liver disease, or having a symptom any of the foregoing, wherein the method comprises administering to the patient in need thereof a therapeutically effective amount of a pharmaceutical composition described herein to treat the condition.

In some embodiments, the present disclosure provides the pharmaceutical composition for administration, including subcutaneous and intravenous administration. The method further includes administering a therapeutically effective amount of the pharmaceutical composition to the patient by way of a pump device. In certain embodiments, the pump device is a patch device for parenteral administration of the composition. In another embodiment, the pharmaceutical composition is administered to the patient using an injection device. The injection device is an auto injector device. In various embodiments, the pharmaceutical composition is administered to the patient subcutaneously or intravenously using the patch device or the auto injector device.

The foregoing as well as other features and advantages of the present disclosure will be more fully understood from the following description, examples, and claims.

DETAILED DESCRIPTION

Figure 1:
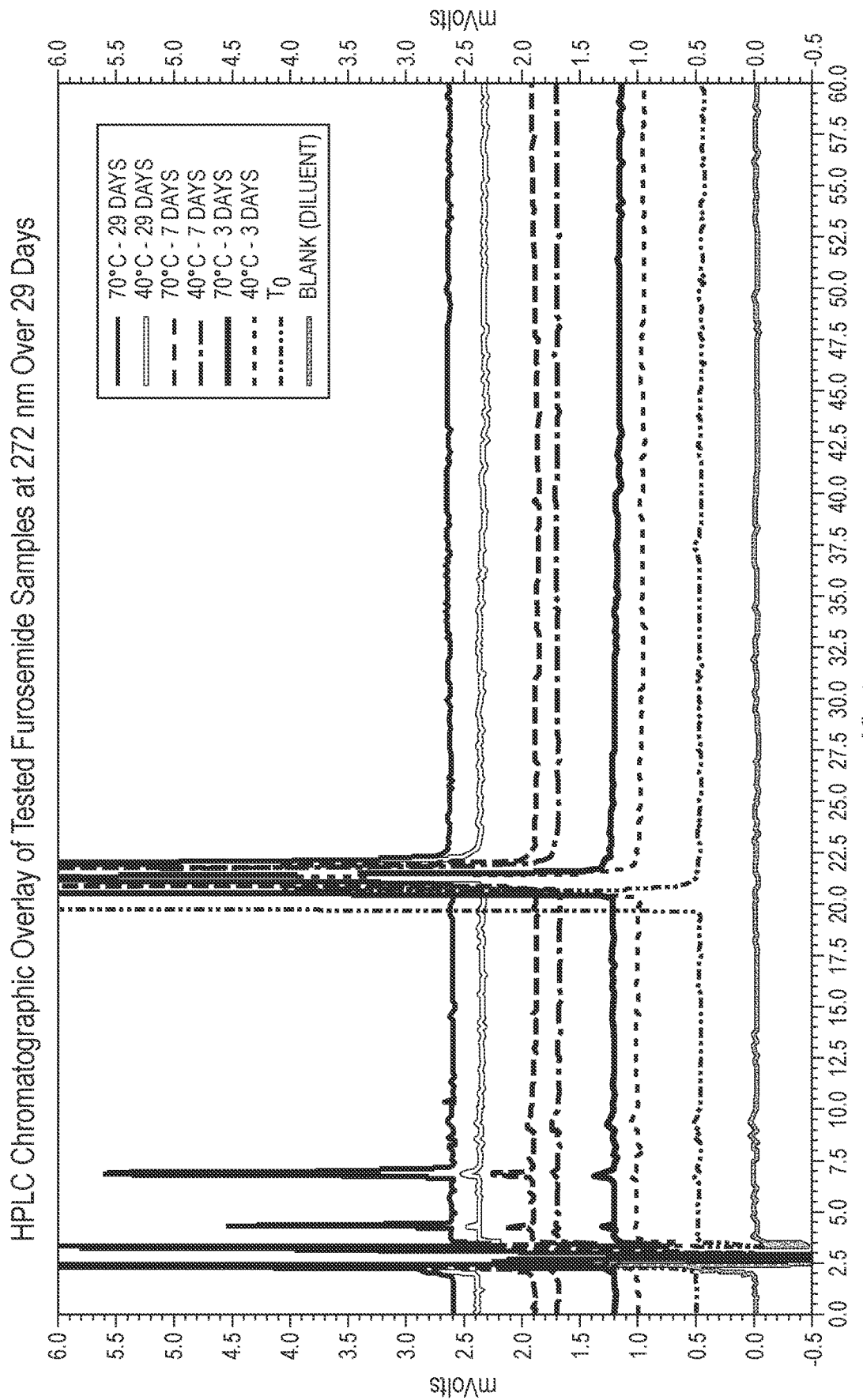
FIG. 1 depicts HPLC chromatograms for analyzed samples of furosemide formulations (where analyte detection analysis was performed at 272 nm), as further described in Example 2.

The present disclosure in this application includes multiple illustrations of the invention. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention.

The use of the terms "include," "includes", "including," "have," "has," or "having," "comprise," "comprises," "comprising" or the like should be generally understood as open-ended and non-limiting unless specifically stated otherwise.

The present disclosure includes pharmaceutical compositions of furosemide at higher concentration and methods of administering the pharmaceutical compositions parenterally. More specifically, the present teachings provide the pharmaceutical compositions having the furosemide and Tris at a concentration of less than or equal to 40 mM in the pharmaceutical composition at a pH value between about 8.0 to about 8.5. The pharmaceutical composition is suitable for parenteral administration, more specifically, suitable for subcutaneous and intravenous administration. Such methods and pharmaceutical compositions can be useful in the treatment of edema, hypertension or heart failure in a patient having or exhibiting symptoms of such conditions.

As used herein, "furosemide" refers to a compound having the formula $C_{12}H_{10}ClN_2O_5S$ or $C_{12}H_{11}ClN_2O_5S$ and pharmaceutically acceptable salts, hydrates and esters thereof, for example, furosemide sodium salt ($C_{12}H_{10}ClN_2NaO_5S$) and furosemide quaternary ammonium salts or any of the amino acid salts including basic amino acids of natural origin such as ornithine, lysine and arginine, which shall include L-arginine, DL-arginine, L-lysine, DL-lysine, L-ornithine, DL-ornithine, or histidine and any variations thereof. Furosemide can be referred to by other names, such as frusemide, 5-(aminosulphonyl)-4-chloro-2-[(2-furanyl-methyl)amino]benzoic acid, or its IUPAC name, 4-chloro-2-((furan-2-ylmethyl)amino)-5-sulfamoylbenzoic acid, or its common trade names, such as Lasix, Furosemid and Furanthril. It is understood that "furosemide" will further refer to any precursor or metabolite, such as 4-chloro-N-furyl-5-sulfamoyl-anthranylic acid as may be required for administration.

As used herein, "Tris(hydroxymethyl)aminomethane" can be referred to as "TRIS," "Tris," "Tris base," "Tris buffer," "Trometamol," "2-Amino-2-(hydroxymethyl)-1,3-propanediol," "Trisamine," "Tromethamine," "Tromethane," "THAM," and tris(hydroxymethyl)aminomethane buffer. In addition, many buffers and/or buffer systems include Tris. For example, Tris-buffered saline ("TBS"), Tris-hydrochloride buffer ("Tris-HCl"), Tris base (pH 10.6), Tris/borate/ethylene diamine tetra-acetate ("EDTA") buffer ("TBE"), and Tris/acetate/EDTA buffer ("TAE"). Tris base is often used with Tris-HCl to prepare Tris buffers at a desired pH. In addition, the present teachings include Tris-related compounds, for example, compounds derived from Tris or structurally-related to Tris, that can act as buffer.

As used herein, "preventing or treating" refers to partially or completely alleviating and/or ameliorating the condition and/or symptoms thereof, and/or preventing its re-occurrence or halting its progression. The present disclosure accordingly includes a method of providing to the patient a combination product that includes a compound or therapeutic composition of the present disclosure in combination or association with a pharmaceutically acceptable carrier, solubilizer or an appropriate buffer.

As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

As used herein, "therapeutically effective" refers to a substance or an amount that elicits a desirable biological activity or effect, reducing or arresting disease processes. For example, a "therapeutically effective amount" of a composition can deliver a dose (also referred to as a "therapeutic dose") sufficient to elicit the desired biological response. In the present invention, the desired biological response is "treating" of edema, heart failure, kidney or liver disease or having symptoms thereof. As used herein, "treating" refers to partially or completely alleviating and/or ameliorating the condition and/or symptoms thereof.

As used herein, "administration" refers to parenteral including intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion, unless specifically mentioned. Specifically, the pharmaceutical composition of the present teachings can be administered parenterally including infusion, injection or implantation, which includes subcutaneous and intravenous administration. When administered for the treatment of a disease state or disorder, it is understood that an effective dosage can vary depending upon many factors such as the compound or therapeutic composition utilized, the mode of administration, and severity of the condition being treated, as well as the various physical factors related to the individual being treated. In therapeutic applications, a compound or therapeutic composition of the present disclosure can be provided to a patient already suffering from a disease, for example, edema related disorders, in an amount sufficient to at least partially ameliorate the symptoms of the disease and its complications and halt or slow down the disease progression. If administered to a patient suffering from the condition prior to clinical manifestation, the administration of a therapeutic composition may prevent the first clinical manifestation or delay its onset.

As used herein, "patient" refers to a mammal, such as a human.

As used herein, the term "about" refers to a ±10% variation from the nominal value unless otherwise indicated or inferred. For example, in certain applications, such as pH measurements, the term "about" can refer to a ±5%, or a ±2.5%, or a ±1% variation from the nominal value or a fixed variation from the nominal value, for example, ±0.1 pH units or ±0.2 pH units.

The present teachings provide the pharmaceutical compositions that include the furosemide or a therapeutic combination including furosemide, and one or more pharmaceutically acceptable carriers, excipients, or diluents such as a buffer. The excipients may include sodium chloride, sodium hydroxide, water, glycerol, mannitol, sodium phosphate, sodium carbonate, lactose, dextrose and other electrolytes.

Examples of such carriers are well known to those skilled in the art and can be prepared in accordance with acceptable pharmaceutical procedures, such as, for example, those described in Remington: The Science and Practice of Pharmacy, 20th edition, ed. Alfonso R. Gennaro (Lippmcott Williams & Wilkins, Baltimore, MD (2000)). For example, liquid media or liquid carriers (which are used interchangeably herein) can be used in preparing the pharmaceutical compositions of the present teachings such as solutions, suspensions, and emulsions. A compound described herein can be dissolved or suspended in a pharmaceutically acceptable liquid carrier such as a buffer, an organic solvent, and/or pharmaceutically acceptable oils and/or fats.

The pharmaceutical compositions of the present teachings can include other suitable pharmaceutical additives such as solubilizers, emulsifiers, buffers, preservatives, suspending agents, thickening agents, colors, viscosity regulators, stabilizers, adsorbents, binders, antioxidants, bulking agents, pH adjusting agents, preservative, solvent, fluidizing agents and osmo-regulators. As the present teachings provide the pharmaceutical compositions and their intended use is with the patients, each of the ingredients or compounds of the pharmaceutical compositions described herein can be a pharmaceutically acceptable ingredient or compound.

The use of the singular herein includes the plural (and vice versa) unless specifically stated otherwise.

It is understood that the order of steps or order for performing certain actions can be changed so long as the intended result is obtained. Moreover, two or more steps or actions may be conducted simultaneously.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

Pharmaceutical Compositions Containing Furosemide

The present disclosure relates to pharmaceutical compositions of furosemide for parenteral administration, more specifically, subcutaneous and intravenous administration. The specific concentration of the Tris less than or equal to about 40 mM defined in the present disclosure and the pH values achieved from about 8.0 to about 8.5 enables the administration of the pharmaceutical composition containing a higher concentration of the furosemide. As such, one advantage of the disclosure is that a higher concentration of the furosemide can be administered to the patient in need thereof. Another advantage of the present disclosure is the ability to administer a therapeutic dose of the furosemide such as 80 mg within the standardized volume of a common cartridge used in a patch pump, i.e., 3-5 mL, to the patient using a patch pump. Yet another advantage of the present disclosure is that the pharmaceutical composition remains stable at the pH value of from about 8.0 to about 8.5 and is compatible for the administration at a higher concentration of the furosemide. Yet another advantage of the present disclosure is that the molar ratio of the Tris to the furosemide is maintained from 1 to 1.5 in the pharmaceutical composition to reduce the osmolarity when compared to pharmaceutical compositions containing a molar ratio of 2 or higher.

The present disclosure relates to the pharmaceutical composition of the furosemide. The furosemide can be present as furosemide or in the form of any variations of analogs, such as a pharmaceutically acceptable salt, hydrate or an ester. The amount of the furosemide in the composition is from about 10 mg/mL to about 30 mg/mL. In some embodiments, the amount of the furosemide is from about 16 mg/mL to about 26 mg/mL. The pharmaceutical composition further contains the Tris at a concentration of less than or equal to 40 mM and maintaining a pH value of the pharmaceutical composition from about 8.0 to about 8.5.

In an embodiment, molar ratio of the Tris to the furosemide in the pharmaceutical composition is less than or equal to 1.5. In another embodiment, the molar ratio of the Tris to the furosemide is less than or equal to 0.8. In yet another embodiment, the molar ratio of the Tris to the furosemide is from about 0.8 and about 1.5. In another embodiment, the molar ratio of the Tris to the furosemide is from about 1 and about 1.5. In one embodiment, the pH value of the pharmaceutical composition is maintained from about 8.2 to about 8.5.

In certain embodiments, the amount of the furosemide in the pharmaceutical composition is from about 16 mg/mL to about 20 mg/mL and the Tris is included in the pharmaceutical composition at a concentration less than or equal to 40 mM. The pH value of the pharmaceutical composition is maintained from about 8.2 to about 8.5 with the molar ratio of the Tris to the furosemide from about 1 to about 1.5. One advantage of the combination of the ingredients in the disclosed amounts and at the disclosed conditions is that therapeutic dose of the furosemide such as 80 mg can be accommodated within a standard size cartridge of the patch pump, e.g., 3-5 mL, and administered to the patient, or self-administered by the patient using, e.g., the patch pump.

In some embodiments, the amount of the furosemide in the pharmaceutical composition is from about 16 mg/mL to about 20 mg/mL. In certain embodiments, the concentration of the Tris in the pharmaceutical composition is less than or equal to 40 mM. In certain embodiments, the pH value of the pharmaceutical composition is from about 8.2 to about 8.5. In certain embodiments, the molar ratio of the Tris to the furosemide is from about 1 to about 1.5. In yet another embodiment, the above pharmaceutical composition is administered to the patient subcutaneously or intravenously as needed.

The pharmaceutical composition of the present disclosure contains the furosemide at higher concentrations and a lower concentration of the Tris, which advantageously enables administration of a higher dose of the furosemide in lower volume of the pharmaceutical composition. The pharmaceutical composition of the present disclosure achieves the administration of the higher concentration of the furosemide at a pH value that is compatible for administration to the patient. More specifically, the pharmaceutical composition is stable and suitable for subcutaneous and intravenous administration.

In some embodiments, the present disclosure includes the pharmaceutical composition of the furosemide at a higher concentration in a drug volume of 2-10 mL. In another embodiment, the concentration of the Tris in the composition is less than or equal to 40 mM. In yet another embodiment, the pharmaceutical composition has the pH value from about 8.0 to about 8.5 compatible for subcutaneous and intravenous administration.

An exemplary embodiment of the present disclosure provides a pharmaceutical composition, comprising: from about 60 mM to about 95 mM of a diuretic selected from the group consisting of 4-chloro-2-((furan-2-ylmethyl)amino)-5-sulfamoylbenzoic acid, a pharmaceutically acceptable salt thereof, and a mixture of the foregoing; from about 20 mM to about 30 mM of a buffer comprising tris(hydroxymethyl)aminomethane; and water; wherein the pharmaceutical composition has a pH value from about 8.0 to about 8.5. In some embodiments, the pharmaceutical composition comprises from about 80 mM to about 95 mM of the diuretic. In some embodiments, the pharmaceutical composition comprises about 91 mM of the diuretic. In some embodiments, the diuretic is a mixture of 4-chloro-2-((furan-2-ylmethyl)amino)-5-sulfamoylbenzoic acid and a pharmaceutically acceptable salt thereof. In some embodiments, the pharmaceutical composition comprises about 25 mM of a buffer comprising tris(hydroxymethyl)aminomethane. In some embodiments, said buffer is a mixture of tris(hydroxymethyl)aminomethane and a pharmaceutically acceptable salt thereof. In some embodiments, the pharmaceutical composition has a pH of from about 8.2 to about 8.5.

Another exemplary embodiment of the present disclosure provides a pharmaceutical composition, comprising: about 91 mM of a diuretic selected from the group consisting of 4-chloro-2-((furan-2-ylmethyl)amino)-5-sulfamoylbenzoic acid, a pharmaceutically acceptable salt thereof, and a mixture of the foregoing; about 25 mM of a buffer comprising tris(hydroxymethyl)aminomethane; and water; wherein the pharmaceutical composition has a pH value from about 8.0 to about 8.5. In a more specific embodiment, the present disclosure provides a pharmaceutical composition, comprising: about 91 mM of a diuretic selected from the group consisting of 4-chloro-2-((furan-2-ylmethyl)amino)-5-sulfamoylbenzoic acid, a pharmaceutically acceptable salt thereof, and a mixture of the foregoing; about 25 mM of a buffer comprising tris(hydroxymethyl)aminomethane and a pharmaceutically acceptable salt thereof; and water; wherein the pharmaceutical composition has a pH value from about 8.0 to about 8.5.

The pharmaceutical composition may be further characterized according to the amount of water in the pharmaceutical composition. In certain embodiments, pharmaceutical composition comprises at least 90% (w/w), 91% (w/w), 92% (w/w), 93% (w/w), 94% (w/w), 95% (w/w), 96% (w/w), 97% (w/w), 98% (w/w), or 99% (w/w) water. In certain embodiments, pharmaceutical composition comprises at least 97% (w/w) water. In certain embodiments, pharmaceutical composition comprises at least 98% (w/w) water. In certain embodiments, pharmaceutical composition comprises at least 99% (w/w) water.

The pharmaceutical composition may be further characterized according to stability of the pharmaceutical composition to storage. For example, in certain embodiments, less than 4% of the diuretic degrades upon storage of the pharmaceutical composition at 40° C. for 29 days. In certain embodiments, less than 1% of the diuretic degrades upon storage of the pharmaceutical composition at 40° C. for 29 days. In certain embodiments, less than 0.5% of the diuretic degrades upon storage of the pharmaceutical composition at 40° C. for 29 days. In certain embodiments, less than 0.1% of the diuretic degrades upon storage of the pharmaceutical composition at 40° C. for 29 days. In certain embodiments, less than 10% of the diuretic degrades upon storage of the pharmaceutical composition at 70° C. for 29 days. In certain embodiments, less than 7% of the diuretic degrades upon storage of the pharmaceutical composition at 70° C. for 29 days. In certain embodiments, less than 5% of the diuretic degrades upon storage of the pharmaceutical composition at 70° C. for 29 days. In certain embodiments, less than 3% of the diuretic degrades upon storage of the pharmaceutical composition at 70° C. for 29 days. In certain embodiments, less than 1% of the diuretic degrades upon storage of the pharmaceutical composition at 70° C. for 29 days. In certain embodiments, less than 3% of the diuretic degrades upon storage of the pharmaceutical composition at 25° C. for 24 months. In certain embodiments, less than 2% of the diuretic degrades upon storage of the pharmaceutical composition at 25° C. for 24 months. In certain embodiments, less than 1% of the diuretic degrades upon storage of the pharmaceutical composition at 25° C. for 24 months. In certain embodiments, less than 0.5% of the diuretic degrades upon storage of the pharmaceutical composition at 25° C. for 24 months. In certain embodiments, less than 0.1% of the diuretic degrades upon storage of the pharmaceutical composition at 25° C. for 24 months. In certain embodiments, less than 0.05% of the diuretic degrades upon storage of the pharmaceutical composition at 25° C. for 24 months.

Additionally, in certain embodiments, the pharmaceutical composition is characterized by the purity of the diuretic in the pharmaceutical composition upon storage. For example, in certain embodiments, the after storage of the pharmaceutical composition at 40° C. for 29 days the diuretic has a purity of at least 97%. In certain embodiments, after storage of the pharmaceutical composition at 40° C. for 29 days the diuretic has a purity of at least 98%. In certain embodiments, after storage of the pharmaceutical composition at 40° C. for 29 days the diuretic has a purity of at least 99%. In certain embodiments, after storage of the pharmaceutical composition at 40° C. for 29 days the diuretic has a purity of at least 99.5%. In certain embodiments, after storage of the pharmaceutical composition at 40° C. for 29 days the diuretic has a purity of at least 99.9%. In certain embodiments, the after storage of the pharmaceutical composition at 70° C. for 29 days the diuretic has a purity of at least 95%. In certain embodiments, after storage of the pharmaceutical composition at 70° C. for 29 days the diuretic has a purity of at least 97%. In certain embodiments, after storage of the pharmaceutical composition at 70° C. for 29 days the diuretic has a purity of at least 98%. In certain embodiments, after storage of the pharmaceutical composition at 70° C. for 29 days the diuretic has a purity of at least 99%. In certain embodiments, after storage of the pharmaceutical composition at 70° C. for 29 days the diuretic has a purity of at least 99.5%. In certain embodiments, the after storage of the pharmaceutical composition at 25° C. for 24 months the diuretic has a purity of at least 97%. In certain embodiments, after storage of the pharmaceutical composition at 25° C. for 24 months the diuretic has a purity of at least 98%. In certain embodiments, after storage of the pharmaceutical composition at 25° C. for 24 months the diuretic has a purity of at least 99%. In certain embodiments, after storage of the pharmaceutical composition at 25° C. for 24 months the diuretic has a purity of at least 99.5%. In certain embodiments, after storage of the pharmaceutical composition at 25° C. for 24 months the diuretic has a purity of at least 99.9%.

Additionally, in certain embodiments, the pharmaceutical composition is characterized by having less than 2% (w/w) of the Peak A component (as described in Example 2 herein) upon storage of the pharmaceutical composition 70° C. for 29 days. In certain embodiments, the pharmaceutical composition is characterized by having less than 1% (w/w) of the Peak A component (as described in Example 2 herein) upon storage of the pharmaceutical composition 70° C. for 29 days. In certain embodiments, the pharmaceutical composition is characterized by having less than 4% (w/w) of the Peak B component (as described in Example 2 herein) upon storage of the pharmaceutical composition 70° C. for 29 days. In certain embodiments, the pharmaceutical composition is characterized by having less than 3% (w/w) of the Peak B component (as described in Example 2 herein) upon storage of the pharmaceutical composition 70° C. for 29 days. In certain embodiments, the pharmaceutical composition is characterized by having less than 2% (w/w) of the Peak B component (as described in Example 2 herein) upon storage of the pharmaceutical composition 70° C. for 29 days.

Another aspect of the disclosure provides a unit container comprising a pharmaceutical composition described herein. In certain embodiments, the container contains from about 5 to about 10 mL of pharmaceutical composition. In certain embodiments, the container contains from about 8 to about 10 mL of pharmaceutical composition.

Therapeutic Applications

In another embodiment, the present disclosure includes a method of treating the patient with or exhibiting symptoms of edema, heart failure, kidney or liver disease by administering to the patient the pharmaceutical composition containing about 10 mg/mL to about 30 mg/mL of the furosemide, or the pharmaceutically acceptable salt, hydrate or ester thereof. The pharmaceutical composition further contains the Tris at a concentration of less than or equal to 40 mM of the furosemide in the pharmaceutical composition.

In another embodiment, the present disclosure provides a method of treating a patient suffering from a condition selected from edema, heart failure, kidney disease, or liver disease, or having a symptom any of the foregoing, wherein the method comprises administering to the patient in need thereof a therapeutically effective amount of a pharmaceutical composition described herein to treat the condition. In certain embodiments, the condition is edema. In certain embodiments, the condition is heart failure. In certain embodiments, the condition is kidney disease or liver disease. In certain embodiments, the condition is kidney disease. In certain embodiments, the condition is liver disease.

In one embodiment, the pharmaceutical composition is administered to the patient subcutaneously. Specifically, the pharmaceutical composition is administered to the patient subcutaneously using a pump device or an injection device. The pump device can include, for example, a patch device. The injection device can include, for example, an auto injector device. In another embodiment, the pharmaceutical composition is administered to the patient intravenously. Specifically, the pharmaceutical composition is administered to the patient intravenously using the pump device or the injection device. In various embodiments, the pharmaceutical composition is administered to the patient subcutaneously or intravenously using the patch device or the auto injector device.

In some embodiments, the present disclosure includes the method of treating the patient with or exhibiting symptoms of edema, heart failure, kidney or liver disease by administering to the patient the pharmaceutical composition of furosemide, or the pharmaceutically acceptable salt, hydrate or furosemide ester with an amount of the furosemide in the composition from about 16 mg/mL to about 20 mg/mL. The composition further contains the Tris at a concentration of 40 mM with the molar ratio of the Tris to the furosemide is from about 1.0 and 1.5 and at the pH value of the pharmaceutical composition is from about 8.2 and about 8.5.

In one embodiment, the patient suffering from edema, heart failure, kidney or liver disease or exhibiting such symptoms thereof is administered with the pharmaceutical composition with the amount of the furosemide from about 16 mg/mL to about 20 mg/mL. In another embodiment, the concentration of the Tris in the pharmaceutical composition is less than or equal to 40 mM. In another embodiment, the pH of the pharmaceutical composition is from about 8.2 to about 8.5. In yet another embodiment, the molar ratio of the Tris to the furosemide is from about 1 to about 1.5.

In some embodiments, the pharmaceutical composition is administered to the patient parenterally including subcutaneous or intravenous administration. In the present disclosure, several devices can be used to facilitate self-administration of the pharmaceutical composition. The device typically includes a reservoir or a cartridge, for example, pre-loaded with, the pharmaceutical composition to be administered. For example, a micropump can provide precise parenteral administration of desired quantities of a liquid pharmaceutical composition. Another type of device useful for parenteral delivery or administration of pharmaceutical composition is often referred to as the pump device or the injection device.

In some embodiments, the present disclosure includes medical devices of a unitary construction. Such medical devices can be for a single use. In certain embodiments, the medical device can be of a multi-piece construction. In such medical devices, a disposable or a reusable portion or component can be present. For example, a housing defining or including the reservoir can be a disposable or a reusable component of the medical device.

The patch pump or patch device of the present disclosure may include a pump device having a drug reservoir and electrolytically, manually, mechanically, automatically or electronically driven piston. The drug pump device may be furnished with a prefilled cartridge. If a glass cartridge or cartridge of other suitable pharmaceutical-grade composite material is used, the drugs can be stored in the pump device for long-term shelf life. The drug pump device may be implantable or include an adhesive patch for adhesion to patient's skin.

Additional Exemplary Features of Pharmaceutical Compositions Containing Furosemide and Therapeutic Applications The pharmaceutical forms of the present disclosure suitable for injection can include sterile aqueous solutions or dispersions for the extemporaneous preparation of sterile injectable solutions or dispersions. In certain embodiments, the pharmaceutical form is sterile, and its viscosity permits it to flow through a syringe. The pharmaceutical form should be stable under the conditions of manufacture and storage, for example, preserved against the contaminating action of microorganisms, if needed. The carrier can be a solvent or dispersion medium containing liquids such as water, ethanol, polyol (e.g., glycerol, propylene glycol, and liquid polyethylene glycol), suitable mixtures thereof, and vegetable oils.

In the present disclosure, the pharmaceutical compositions can achieve higher level of the furosemide suitable for administration. For example, the amount of the furosemide in the pharmaceutical composition can be about 5 mg/mL or greater, about 8 mg/mL or greater, or about 10 mg/mL or greater. In various embodiments, the amount of the furosemide can be about 15 mg/mL or greater, about 10 mg/mL or greater, about 20 mg/mL or greater, or about 20 mg/mL, or about 22 mg/mL or about 23 mg/mL or greater.

In some embodiments, the furosemide can be present in an amount from about 10 mg/mL to about 30 mg/mL, from about 10 mg/mL to about 20 mg/mL, from about 10 mg/mL to about 15 mg/mL, from about 15 mg/mL to about 30 mg/mL, from about 16 mg/mL to about 26 mg/mL, or from about 20 mg/mL to about 30 mg/mL. In some embodiments, the furosemide can be present in an amount from about 25 mg/mL to about 30 mg/mL.

In the present disclosure, furosemide, therapeutic combinations, and pharmaceutical compositions can be useful for treating a pathological condition or disorder or symptoms in the patient. The present disclosure provides administering higher concentrations of the furosemide parenterally to alleviate the disorders, such as edema, heart failure, kidney or liver disease or having such symptoms. The present teachings accordingly include the method of providing to the patient the pharmaceutical composition that includes a compound or therapeutic combination of the present teachings in combination or association with a pharmaceutically acceptable carrier or solubilizer or a suitable buffer. Compounds and therapeutic combinations of the present teachings can be administered alone or in combination with other therapeutically effective compounds or therapies for the treatment of a pathological condition or disorder.

The present disclosure also includes the methods of administration of the pharmaceutical composition including the furosemide or one or more of its analogues or variations or precursors to the patient with edema related disease or disorder. The edema related disease or disorder may also include heart failure, chronic kidney disease.

In certain embodiments, the pharmaceutical composition can have the pH value in the range of from about 8.0 to about 8.5. In certain embodiments, the pharmaceutical formulations can have the pH value in the range of from about 8.2 to about 8.5, or from about 8.3 to about 8.5. In some embodiments, the pharmaceutical composition can have the pH value in the range of from about 8.4 to about 9.0, from about 8.4 to about 8.8, or from about 8.4 to about 8.6.

In various embodiments, the molar ratio of the Tris to the furosemide in the pharmaceutical composition can be greater than about 0.5, or greater than about 0.65, or greater than about 2, or greater than about 1.5, or greater than about 3. In certain embodiments, the molar ratio of the Tris to the furosemide can be less than equal to about 0.8, or between about 1.0 to about 1.5.

Further, in various embodiments, the Tris in the pharmaceutical composition can be less than or equal to about 40 mM. In some embodiments, the concentration of the Tris can be less than or equal to about 35 mM, less than or equal to about 30 mM, or less than or equal to about 25 mM. In certain embodiments, the concentration of the Tris can be in a range of from about 5 mM to about 40 mM, from about 40 mM to about 45 mM, from about 40 mM to about 47 mM, from about 20 mM to about 40 mM, or from about 20 mM to about 30 mM. In certain embodiments, the concentration of the Tris can be from about 10 mM or about 40 mM.

In the present disclosure, the pharmaceutical composition may reduce the disease condition and symptoms by at least about 5% to at least about 99% as compared to an untreated patient. The compound may be administered to the patients in various forms including, an injection, a transdermal patch, sustained-release formulations and the like. The composition may be administered via enteral or parenteral route including, intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion.

The typical dosages of the compounds and the compositions of the present disclosure may vary within a wide range depending on many factors, including but not limited to, route of administration, treatment stage, pretreatment use of oral medications, body weight, age and general condition of the patient.

The pharmaceutical composition of the present disclosure may also contain adjuvants, diluents, excipients and/or carriers, known in the art, compatible with the compounds and the other ingredients of the pharmaceutical composition, and not deleterious to the recipient thereof.

Various embodiments of the present disclosure enable administration of higher concentrations of the furosemide in a lower dose of the pharmaceutical composition to the patient. Further, the present disclosure includes a lower concentration of the Tris in the pharmaceutical composition enhancing the stability of the pharmaceutical composition. Further, the pharmaceutical composition of various embodiments of the present disclosure has the pH appropriate for subcutaneous or intravenous administration of the composition to the patient.

Another advantage of the embodiments of the present disclosure is that the molar ratio of the Tris to the furosemide in the pharmaceutical composition is from about 1 to about 1.5. Yet another advantage of the embodiments of the present disclosure is that the pharmaceutical compositions with higher concentration of the furosemide and lower concentration of the Tris can be administered with the pump device or the injection device.

Medical Kits

Another aspect of the invention provides a medical kit comprising, for example, (i) a pharmaceutical composition described herein, and (ii) instructions for use, such as for use in a method described herein.

It is understood that the examples, embodiments and teachings presented in this application are described merely for illustrative purposes. Any variations or modifications thereof are to be included within the scope of the present application as discussed.

EXAMPLES

The invention now being generally described, will be more readily understood by reference to the following examples, which are included merely for purposes of illustration of certain aspects and embodiments of the present invention, and are not intended to limit the invention.

Example 1—Preparation of Exemplary Aqueous Furosemide Formulation

An exemplary aqueous furosemide formulation was prepared according to the procedure set forth below. The aqueous furosemide formulation contained furosemide at a concentration of 30 mg/mL and tris(hydroxymethyl)aminomethane buffer at a concentration of 25 mM. The formulation had a pH of 8.3.

Tris(hydroxymethyl)aminomethane (Tris) buffer solution (where the concentration of Tris buffer was 25 mM) was prepared by dissolving 1.8388 g (11.7 mM) Tris-HCl (Roche, Product No. 10812846001) and 1.6090 g (13.2 mM) Tris free-base (Roche, Product No. 10708976001) in 1 liter of purified water (EMD, HPLC water, Product No. WX0008-1) in a volumetric flask. The resulting Tris buffer solution was filtered through a 0.2 µm nylon filter, and then a 200 mL aliquot of the filtered solution was added to 0.7471 g (0.374% w/v) of sodium hydroxide (Alfa Aesar, Product No. 87003-294) in a glass bottle. The bottle was shaken until the solid was fully dissolved, and the resulting solution was filtered through a 0.2 µm nylon filter, to afford basified Tris buffer solution.

To 3.0541 g of furosemide (USP grade, Spectrum, Product No. F1133) in an amber, 100-mL volumetric flask was added 95 mL of the basified Tris buffer solution. The mixture was sonicated until the solid fully dissolved. Additional basified Tris buffer solution was added to reach a total volume of 100 mL. The pH of the solution was adjusted to pH 8.3 by the addition of a 10 N NaOH solution (27 µL) to provide the final furosemide formulation.

The osmolality of the final furosemide solution was measured to be 171 mOsm/kg.

Example 2—Stability Analysis of Exemplary Furosemide Formulation

A stability analysis was conducted on the furosemide formulation prepared according to the procedure in Example 1. Experimental procedures and results are provided below Part I—Experimental Procedures Aliquots of the furosemide formulation (2.6 mL) were added to 3-mL glass vials, and the vials were sealed and crimped. Then, the vials were stored protected from light in ovens at 40° C. and 70° C. for a specified duration of time (e.g., 29 days). After storage for either 3 days, 7 days, or 29 days, a vial was removed from the oven and the furosemide formulation was analyzed for visual appearance, pH, and to determine the amount of furosemide and/or impurities in the formulation. Analysis of impurities included determination of the amount of an impurity designated Peak A and an impurity designated as Peak B in the HPLC chromatogram.

Analysis by HPLC was conducted according to the United States Pharmacopeia and National Formulary (USP-NF) method described in Table 1, below, following serial dilutions of the formulations (first dilution: 0.1 mL formulation+0.9 mL diluent; second dilution: 0.01 mL first dilution+0.99 mL diluent).

Part II—Results

Figure 2:
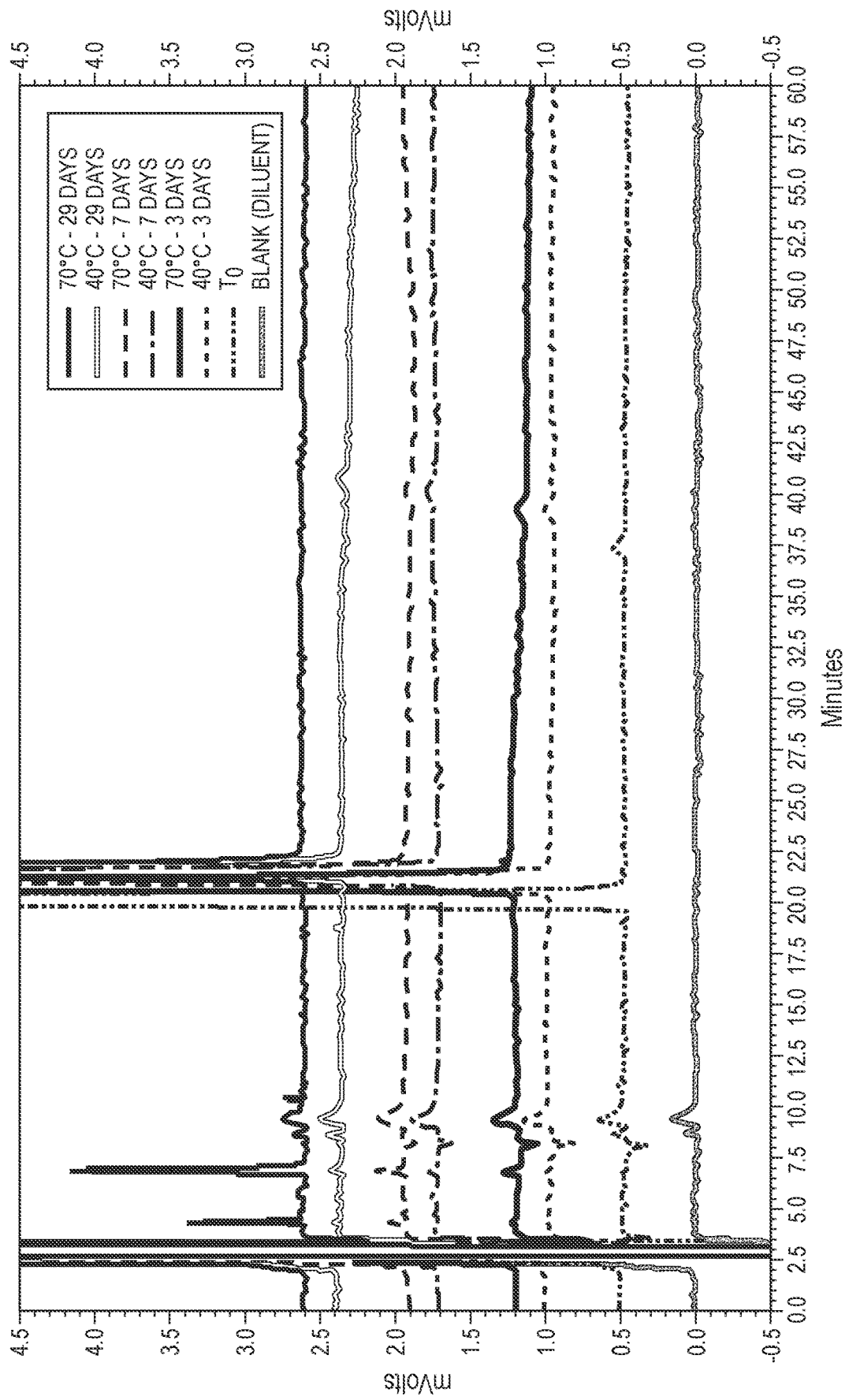
FIG. 2 depicts HPLC chromatograms for analyzed samples of furosemide formulations (where analyte detection analysis was performed at 254 nm), as further described in Example 2.

Results of the stability analysis are provided in Table 2 and Table 3 below. Representative HPLC chromatograms for analyzed samples of furosemide formulation are depicted in FIG. 1 (analyte detection analysis was performed at 272 nm) and FIG. 2 (analyte detection analysis was performed at 254 nm). All values, other than pH, in Table 2 and Table 3 are the average of results from three HPLC chromatograms obtained from a given sample.

The results demonstrate that the tested furosemide formulation had good stability when stored at 40° C. for 29 days. Minor amounts of decomposition of furosemide were observed when the furosemide formulation was stored at 70° C. for 29 days.

TABLE 1

HPLC Method for Analytical Analysis of Stored Furosemide Formulations

| Column information | Name | Agilent Pursuit XRs 3 C18 4.6 mm × 250 mm |
|---|---|---|
| | Catalog # | 564387 |
| Mobile Phase | | Water:THF:Acetic Acid 70:30:1 |
| Diluent | | 50/50 (v/v) ACN/water containing 2.2% acetic acid |
| Flow rate | | 1.0 mL/min |
| Column temperature | | 40° C. |
| Autosampler temperature | | 5° C. |
| Injection volume | | 20 µL |
| Detector wavelengths | | 254 nm and 272 nm |
| Run time | | 60.0 min |

TABLE 2

Stability Results for Formulation Stored at 40° C.

| Duration of Storage | 0 days | 3 days | 7 days | 29 days |
|---|---|---|---|---|
| Visual Appearance | Clear, colorless solution | Clear, colorless solution | Clear, colorless solution | Clear, colorless solution |
| pH | 8.30 | 8.32 | 8.35 | 8.39 |
| Concentration of Furosemide (mg/mL) | 30.22 ± 0.49 | 29.38 ± 0.27 | 30.24 ± 0.55 | 30.19 ± 0.78 |
| Percent Recovery of Furosemide (%) | N/A | 97.20 ± 0.89 | 100.08 ± 1.81 | 99.90 ± 2.59 |
| Percent Purity of Furosemide (%) (measured at 254 nm) | 99.47 ± 0.05 | 99.50 ± 0.05 | 99.53 ± 0.08 | 99.68 ± 0.03 |
| Percent Peak A $t_R$ ~4.3 min (%) (measured at 254 nm) | Below Detection Limit | Below Detection Limit | Below Detection Limit | Below Detection Limit |
| Percent Peak B $t_R$ ~6.8 min (%) (measured at 254 nm) | 0.05 ± 0.02 | 0.08 ± 0.04 | 0.08 ± 0.00 | 0.12 ± 0.02 |
| Percent Purity of Furosemide (%) (measured at 272 nm) | 99.88 ± 0.01 | 99.89 ± 0.01 | 99.85 ± 0.01 | 99.81 ± 0.01 |

TABLE 2-continued

Stability Results for Formulation Stored at 40° C.

| Duration of Storage | 0 days | 3 days | 7 days | 29 days |
|---|---|---|---|---|
| Percent Peak A $t_R$ ~4.3 min (%) (measured at 272 nm) | Below Detection Limit | Below Detection Limit | 0.02 ± 0.00 | 0.03 ± 0.00 |
| Percent Peak B $t_R$ ~6.8 min (%) (measured at 272 nm) | 0.03 ± 0.00 | 0.03 ± 0.00 | 0.04 ± 0.01 | 0.10 ± 0.00 |

TABLE 3

Stability Results for Formulation Stored at 70° C.

| Duration of Storage | 0 days | 3 days | 7 days | 29 days |
|---|---|---|---|---|
| Visual Appearance | Clear, colorless solution | Clear, colorless solution | Clear, colorless solution | Clear, yellow-brown solution |
| pH | 8.30 | 8.34 | 8.35 | 8.08 |
| Concentration of Concentration (mg/mL) | 30.22 ± 0.49 | 30.11 ± 0.72 | 30.56 ± 0.43 | 28.58 ± 0.29 |
| Percent Recovery of Furosemide (%) | N/A | 99.64 ± 2.38 | 101.13 ± 1.41 | 94.56 ± 0.95 |
| Percent Purity of Furosemide (%) (measured at 254 nm) | 99.47 ± 0.05 | 99.41 ± 0.05 | 99.31 ± 0.02 | 96.41 ± 0.06 |
| Percent Peak A $t_R$ ~4.3 min (%) (measured at 254 nm) | Below Detection Limit | 0.06 ± 0.03 | 0.08 ± 0.02 | 0.74 ± 0.00 |
| Percent Peak B $t_R$ ~6.8 min (%) (measured at 254 nm) | 0.05 ± 0.02 | 0.19 ± 0.02 | 0.28 ± 0.04 | 2.76 ± 0.01 |
| Percent Purity of Furosemide (%) (measured at 272 nm) | 99.88 ± 0.01 | 99.76 ± 0.02 | 99.64 ± 0.02 | 97.07 ± 0.02 |
| Percent Peak A $t_R$ ~4.3 min (%) (measured at 272 nm) | Below Detection Limit | 0.04 ± 0.01 | 0.08 ± 0.00 | 0.76 ± 0.00 |
| Percent Peak B $t_R$ ~6.8 min (%) (measured at 272 nm) | 0.03 ± 0.00 | 0.11 ± 0.01 | 0.22 ± 0.01 | 2.17 ± 0.01 |

Example 3—Preparation and Furosemide Solubility Analysis of Exemplary Aqueous Mixtures An exemplary aqueous furosemide mixtures containing furosemide at a concentration of either 10 mg/mL or 20 mg/mL were prepared according to the procedure set forth below and analyzed for the presence of undissolved furosemide. Experimental procedures and results are provided below.

Part I—Experimental Procedures

An aqueous mixture containing furosemide (10 mg/mL) and Tris buffer (40 mM) was prepared according to the following procedure. Approximately 100.3±0.5 mg of furosemide was weighed into the 20 mL clear vial. In a 10 mL volumetric flask, 48.45±0.5 mg of Tris was added then diluted to the volume with Milli-Q water. The 10 mL Tris buffer solution was then transferred into the above 20 mL vial containing furosemide to make 10 mg/mL furosemide aqueous mixture.

The 10 mg/mL furosemide aqueous mixture was allowed to stir at 20° C. at 1300 rpm for 20 minutes or longer prior to any visual examination and pH measurement. To obtain the targeted pH of 8.0-8.5 for the furosemide aqueous mixture, aliquots of a 1.0 N NaOH solution were added in small increments to the furosemide aqueous mixture. The pH of the resulting furosemide aqueous mixture after NaOH addition was measured along with the visible observation for appearance and solubility estimate.

An aqueous mixture containing furosemide (10 mg/mL) and Tris buffer (40 mM) was prepared according to the following procedure. Approximately 200.3±0.5 mg of furosemide was weighed into the 20 mL clear vial. In a 10 mL volumetric flask, 48.45±0.5 mg of Tris was added and then diluted to the volume with Milli-Q water. The 10 mL Tris buffer solution was then transferred into the above 20 mL vial containing furosemide to make 20 mg/mL furosemide aqueous mixture.

The 20 mg/mL furosemide aqueous mixture was allowed to stir at 20° C. at 1300 rpm for 20 minutes or longer prior to any visual examination and pH measurement. To obtain the targeted pH of 8.0-8.5 for the furosemide aqueous mixture, aliquots of a 1.0 N NaOH solution were added in small increments to the furosemide aqueous mixture. The pH of the resulting furosemide aqueous mixture after NaOH addition was measured along with the visible observation for appearance and solubility estimate.

Part II—Results

Results are provided in Table 1 for the 10 mg/mL furosemide aqueous mixture. Results are provided in Table 2 for the 20 mg/mL furosemide aqueous mixture

TABLE 1

Results from 10 mg/mL Furosemide Aqueous Mixture

| Experiment No. | Volume of NaOH Solution Added (µL) | Presence of Undissolved Furosemide | Time Stirred at 20° C. (mins) | pH of Mixture |
|---|---|---|---|---|
| 1-initial | 0 | No | 20 | 7.44 |
| 2 | 5 | No | 30 | 7.48 |
| 3 | 10 | No | 50 | 7.54 |
| 4 | 30 | No | 960 (16 h) | 7.66 |
| 5 | 30 | No | 20 | 7.83 |
| 6 | 30 | No | 30 | 7.83 |
| 7 | 50 | No | 60 | 8.16 |

TABLE 2

Results from 20 mg/mL Furosemide Aqueous Mixture

| Experiment No. | Volume of NaOH Solution Added (µL) | Presence of Undissolved Furosemide | Time Stirred at 20° C. (mins) | pH of Mixture |
|---|---|---|---|---|
| 1-initial | 0 | Yes | 30 | 6.79 |
| 2 | 100 | Yes | 20 | 6.90 |
| 3 | 100 | Yes | 25 | 6.86 |
| 4 | 100 | No | 20 | 7.67 |
| 5 | 100 | No | 120 (2 hours) | 8.11 |

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition, comprising:
    furosemide, or a pharmaceutically acceptable salt, hydrate or ester thereof; and
    tris(hydroxymethyl)aminomethane; wherein
    the furosemide is present in the pharmaceutical composition at a concentration from about 10 mg/mL to about 30 mg/mL;
    the tris(hydroxymethyl)aminomethane is present in the pharmaceutical composition at a concentration of less than or equal to 40 mM; and
    the pharmaceutical composition has a pH value from about 8.0 to about 8.5;
    wherein the pharmaceutical composition has a molar ratio of the tris(hydroxymethyl)aminomethane to the furosemide of less than or equal to 0.8.

2. The pharmaceutical composition of claim 1, wherein the furosemide is present in the pharmaceutical composition at a concentration from about 25 mg/mL to about 30 mg/mL.

3. The pharmaceutical composition of claim 1, wherein the furosemide is present in the pharmaceutical composition at a concentration of about 30 mg/mL.

4. The pharmaceutical composition of claim 1, wherein the tris(hydroxymethyl)aminomethane is present in the pharmaceutical composition at a concentration of from about 5 mM to about 40 mM.

5. The pharmaceutical composition of claim 1, wherein the tris(hydroxymethyl)aminomethane is present in the pharmaceutical composition at a concentration of less than or equal to about 25 mM.

6. The pharmaceutical composition of claim 3, wherein the tris(hydroxymethyl)aminomethane is present in the pharmaceutical composition at a concentration of from about 20 mM to about 30 mM.

7. The pharmaceutical composition of claim 3, further comprising water.

8. The pharmaceutical composition of claim 4, further comprising water.

9. The pharmaceutical composition of claim 6, further comprising water.

10. The pharmaceutical composition of claim 1, wherein the concentration of the furosemide after storage at 70° C. for 29 days is about 94% of the original furosemide concentration.

11. The pharmaceutical composition of claim 1, wherein the pH of the pharmaceutical composition after storage at 70° C. for 29 days is about 97% of the original pH value.

12. A pharmaceutical composition, comprising:
    from about 60 mM to about 95 mM of a diuretic wherein the diuretic is 4-chloro-2-((furan-2-ylmethyl)amino)-5-sulfamoylbenzoic acid, or a pharmaceutically acceptable salt thereof, or a mixture of the foregoing;
    from about 20 mM to about 30 mM of a buffer comprising tris(hydroxymethyl)aminomethane; and
    water; wherein the pharmaceutical composition has a pH value from about 8.0 to about 8.5.

13. The pharmaceutical composition of claim 12, wherein the pharmaceutical composition comprises from about 80 mM to about 95 mM of the diuretic.

14. The pharmaceutical composition of claim 12, wherein the pharmaceutical composition comprises about 91 mM of the diuretic.

15. The pharmaceutical composition of claim 12, wherein the diuretic is a mixture of 4-chloro-2-((furan-2-ylmethyl)amino)-5-sulfamoylbenzoic acid and a pharmaceutically acceptable salt thereof.

16. The pharmaceutical composition of claim 14, wherein the pharmaceutical composition comprises about 25 mM of a buffer comprising tris(hydroxymethyl)aminomethane.

17. The pharmaceutical composition of claim 12, wherein said buffer is a mixture of tris(hydroxymethyl)aminomethane and a pharmaceutically acceptable salt thereof.

18. The pharmaceutical composition of claim 12, wherein the pharmaceutical composition has a pH of from about 8.2 to about 8.5.

19. The pharmaceutical composition of claim 12, wherein less than 4% of the diuretic degrades upon storage of the pharmaceutical composition at 40° C. for 29 days.

20. The pharmaceutical composition of claim 12, wherein less than 1% of the diuretic degrades upon storage of the pharmaceutical composition at 40° C. for 29 days.

21. The pharmaceutical composition of claim 12, wherein less than 10% of the diuretic degrades upon storage of the pharmaceutical composition at 70° C. for 29 days.

22. The pharmaceutical composition of claim 12, wherein less than 7% of the diuretic degrades upon storage of the pharmaceutical composition at 70° C. for 29 days.

23. A method of treating a patient suffering from edema, heart failure, kidney or liver disease or having symptoms thereof, the method comprising:
    administering to the patient a therapeutically effective amount of a pharmaceutical composition of claim 1.

24. A method of treating a patient suffering from a condition selected from edema, heart failure, kidney disease, or liver disease, or having a symptom any of the foregoing, comprising administering to the patient in need thereof a therapeutically effective amount of a pharmaceutical composition of claim 12 to treat the condition.

25. The method of claim 24, wherein the condition is edema.

26. The method of claim 24, wherein the condition is heart failure.

* * * * *